US00PP15867P2

(12) United States Plant Patent
Lommerse

(10) Patent No.: US PP15,867 P2
(45) Date of Patent: Jul. 19, 2005

(54) ***DAHLIA* PLANT NAMED 'KIEDAHSUY'**

(50) Latin Name: *Dahlia variabilis*
Varietal Denomination: Kiedahsuy

(75) Inventor: Henry Lommerse, Mariahout-Laarbeek (NL)

(73) Assignee: Kieft Bloemzaden B.V., Venhuizen (NL)

( * ) Notice: Subject to any disclaimer, the term of this patent is extended or adjusted under 35 U.S.C. 154(b) by 45 days.

(21) Appl. No.: 10/822,977

(22) Filed: Apr. 13, 2004

(51) Int. Cl.[7] ..... A01H 5/00
(52) U.S. Cl. ..... Plt./321
(58) Field of Search ..... Plt./321

*Primary Examiner*—Anne Marie Grunberg
*Assistant Examiner*—June Hwu
(74) *Attorney, Agent, or Firm*—C. A. Whealy

(57) ABSTRACT

A distinct cultivar of *Dahlia* plant named 'Kiedahsuy', characterized by its upright, compact and rounded plant habit; freely basal branching habit; semi-double type inflorescences; and bright yellow-colored ray and disc florets.

1 Drawing Sheet

Botanical classification/cultivar designation: *Dahlia variabilis* cultivar Kiedahsuy.

BACKGROUND OF THE INVENTION

The present Invention relates to a new and distinct cultivar of *Dahlia* plant, botanically known as *Dahlia variabilis*, commercially referred to as a pot-type *Dahlia*, and hereinafter referred to by the cultivar name Kiedahsuy.

The new *Dahlia* is a product of a planned breeding program conducted by the Inventor in Venhuizen, The Netherlands. The objective of the breeding program is to create new pot-type *Dahlia*, cultivars with desirable inflorescence form and attractive ray and disc floret coloration.

The new *Dahlia* originated from a cross-pollination made by the Inventor in 1999 of a proprietary *Dahlia variabilis* selection identified as code number 98.1833, not patented, as the female, or seed, parent with a proprietary *Dahlia variabills* selection identified as code number 98.3426, not patented, as the male, or pollen, parent. The new *Dahlia* was discovered and selected by the Inventor as a single flowering plant within the progeny of the stated cross-pollination in a controlled environment in Venhuizen, The Netherlands.

Asexual reproduction of the new *Dahlia* by vegetative tip cuttings was first conducted in Mariahout-Laarbeek, The Netherlands since 2000. Asexual reproduction by cuttings has shown that the unique features of this new *Dahlia* are stable and reproduced true to type in successive generations.

SUMMARY OF THE INVENTION

The cultivar Kiedahsuy has not been observed under all possible environmental conditions. The phenotype may vary somewhat with variations in environment such as temperature and daylength, without, however, any variance in genotype.

The following traits have been repeatedly observed and are determined to be the unique characteristics of 'Kiedahsuy'. These characteristics in combination distinguish 'Kiedahsuy' as a new and distinct pot-type *Dahlia:*

1. Upright, compact and rounded plant habit.
2. Freely basal branching habit, full and dense plants.
3. Semi-double type inflorescences.

4. Bright yellow-colored ray and disc florets.
5. Good garden performance.

Compared to plants of the female parent, plants of the new *Dahlia* differ in ray floret coloration as plants of the female parent have pale yellow-colored ray florets. Compared to plants of the male parent plants of the new *Dahlia* differ primarily in ray floret coloration.

Plants of the new *Dahlia* can be compared to plants of the *Dahlia* cultivar Dahlstar Yellow, not patented. In side-by-side comparisons conducted in Venhuizen, The Netherlands, plants of the new *Dahlia* are more compact, more freely branched, flower earlier and have more ray florets per inflorescence than plants of the cultivar Dahlstar Yellow.

BRIEF DESCRIPTION OF THE PHOTOGRAPHS

The accompanying colored photographs illustrate the overall appearance of the new *Dahlia* showing the colors as true as it is reasonably possible to obtain in colored reproductions of this type. Colors in the photographs may differ from the color values cited in the detailed botanical description which accurately describe the colors of the new *Dahlia.*

The photograph at the bottom of the sheet comprises a side perspective view of a typical flowering plant of 'Kiedahsuy'.

The photograph at the top of the sheet is a close-up view of typical inflorescences of 'Kiedahsuy'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown and flowered during the winter and early spring in Lompoc, Calif., under commercial practice in a polycarbonate-covered greenhouse with day temperatures about 18 to 24° C., night temperatures about 16 to 18° C., and light levels about 4,000 to 8,000 foot-candles. Rooted cuttings were planted in 10-cm container and plants had been growing for about ten weeks when the photographs and the description were taken.

Botanical classification: *Dahlia variabilis* cultivar Kiedahsuy.

Parentage:

*Female, or seed, parent.*—Proprietary *Dahlia variabilis* selection identified as code number 98.1833, not patented.

*Male, or pollen, parent.*—Proprietary *Dahlia variabilis* selection identified as code number 98.3426, not patented.

Propagation:

*Type.*—Terminal tip cuttings.

*Time to rooting.*—About two weeks at 21° C.

*Time to develop a rooted cutting.*—About three weeks at 21° C.

*Root description.*—Thick, fleshy, freely branching; development of tubers has not been observed.

Plant description:

*Appearance.*—Herbaceous pot-type *Dahlia.* Inverted triangle; stems mostly upright and somewhat outwardly spreading giving a uniformly rounded appearance to the plant; relatively compact. Freely basal branching, about ten lateral branches per plant; dense and full plants. Moderately vigorous growth habit.

*Plant height, soil level to top of leaf plane.*—About 10 cm.

*Plant height, soil level top of inflorescences.*—About 18 cm.

*Plant width or area of spread.*—About 16 cm.

*Lateral branches.*—Length: About 10 cm. Diameter: About 2.5 mm. Internode length: About 1.3 cm. Strength: Strong. Texture: Smooth, glabrous. Color: 144B.

*Foliage description.*—Arrangement: Opposite; simple. Length: About 5 cm. Width: About 3.8 cm. Shape: Ovate. Apex: Acute. Base: Attenuate. Margin: Serrate. Texture, upper and lower surfaces: Smooth, glabrous. Petiole length: About 1.8 cm. Petiole diameter: About 2.5 mm. Petiole texture, upper and lower surfaces: Smooth, glabrous. Color: Developing foliage, upper surface: 147A. Developing foliage, lower surface: 147B. Fully expanded foliage, upper surface: 146A. Fully expanded foliage, lower surface: 147C. Venation, upper and lower surfaces: 147C. Petiole, upper and lower surfaces: 144A.

Inflorescence description:

*Appearance.*—Terminal and axillary semi-double type inflorescences held above and beyond the foliage on strong flexible peduncles; inflorescences face upright or outwardly. Composite inflorescence form with obovate-shaped ray florets and disc florets massed at the center, ray and disc florets arranged acropetally on a capitulum. Inflorescences not fragrant. Inflorescences persistent.

*Flowering response.*—Plants flower continuous and freely from April until October in Northern Europe.

*Postproduction longevity.*—Inflorescences maintain good color and substance for about seven to ten days on the plant.

*Quantity of inflorescences.*—About twelve inflorescences and inflorescence buds per plant.

*Inflorescence bud.*—Shape: Oblate. Length: About 8 mm. Diameter: About 1 cm. Color: 4A.

*Inflorescence size.*—Diameter: About 7 cm. Depth (height) About 3.5 cm. Diameter of disc: About 1.8 cm. Receptacle height: About 1.5 cm. Receptacle diameter: About 2.4 cm.

*Ray florets.*—Shape: Obovate. Aspect: Straight, concave. Length: About 3 cm. Width: About 1.6 cm. Apex: Rounded to slightly emarginate. Base: Attenuate. Margin: Entire. Texture: Smooth, glabrous; satiny. Number of ray florets per inflorescence: About 58 in about five rows. Color: When opening and fully opened, upper surface: 4A; color becoming closer to 4B. When opening and fully opened, lower surface: 4B.

*Disc florets.*—Shape: Tubular, elongated. Apex: Five-pointed. Length: About 1.3 cm. Width: Apex, about 2.5 mm; base, about 1.5 mm. Number of disc florets per inflorescence: About 84. Color: Immature: 14A. Mature, apex and mid-section: 5B. Mature, base: 4C.

*Involucral bracts.*—Quantity: About 66; imbricate. Length: About 1.2 cm. Width: About 5 mm. Shape: Elliptical. Apex: Rounded Base: Truncate. Margin: Entire. Texture, upper and lower surfaces: Smooth, thin, membranous. Color, upper and lower surfaces: 147A.

*Peduncles.*—Length, terminal peduncle: About 8.5 cm. Length, second peduncle: About 9 cm. Length, third peduncle: About 9.3 cm. Diameter: About 2 mm. Strength: Strong, very flexible. Aspect: Upright to about 30° C. Texture: Smooth, glabrous. Color: 144A.

*Reproductive organs.*—Androecium: Present on disc florets only. Anther color: 23A. Pollen amount: Scarce. Pollen color: 23A. Gynoecium: Present on both ray and disc florets. Stigma color: 12A. Style color: 12C. Ovary color: 150D.

*Seed/fruit.*—Seed and fruit production has not been observed.

Disease/pest tolerance: Plants of the new *Dahlia* have not been observed to be tolerant to pathogens and pests common to *Dahlias.*

Garden performance: Plants of the new *Dahlia* have been observed to be wind and rain-tolerant; and have been observed to be tolerant to temperatures ranging from 5 to 30° C.

It is claimed:

1. A new and distinct cultivar of *Dahlia* plant named 'Kiedahsuy', as illustrated and described.

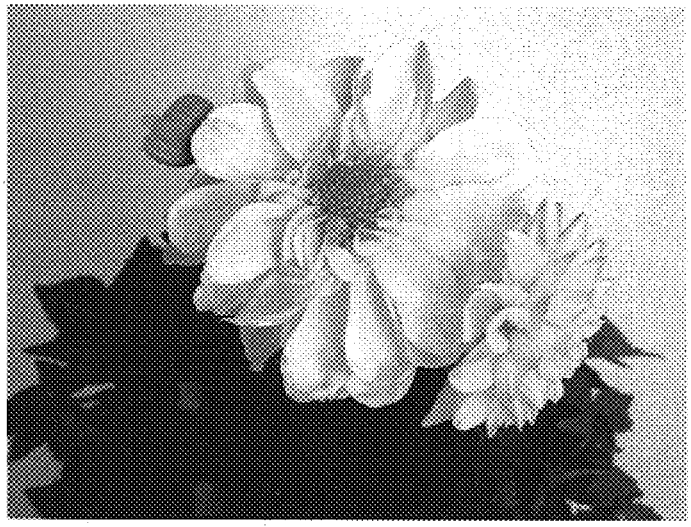
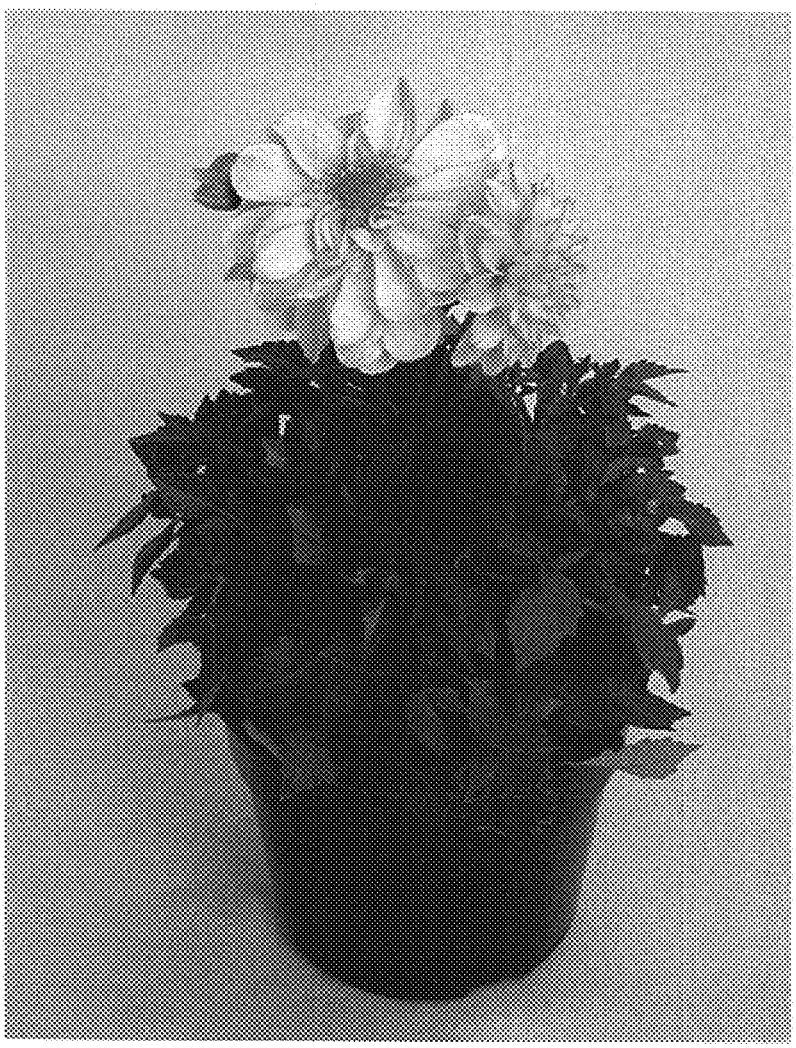

* * * * *